United States Patent [19]

Schoolman

[11] Patent Number: 5,215,539
[45] Date of Patent: Jun. 1, 1993

[54] VACUUM STRIP APPARATUS FOR SURGERY

[75] Inventor: Arnold Schoolman, Kansas City, Mo.

[73] Assignee: Schoolman Scientific Corporation, Kansas City, Mo.

[21] Appl. No.: 256,629

[22] Filed: Oct. 12, 1988

[51] Int. Cl.$^5$ .............................................. A61M 27/00
[52] U.S. Cl. ..................................... 604/280; 604/180; 604/313; 604/317; 604/355
[58] Field of Search .................. 604/73, 264, 280, 281, 604/284, 313, 355, 356, 180, 317

[56] References Cited

U.S. PATENT DOCUMENTS

| | | | |
|---|---|---|---|
| 2,195,771 | 4/1940 | Estler | 604/355 |
| 2,587,910 | 3/1952 | Shulman | 604/284 |
| 2,819,719 | 1/1958 | Utley et al. | 604/284 |
| 3,384,089 | 5/1968 | Shriner | 604/280 |
| 3,537,447 | 11/1970 | Gauthier . | |
| 3,763,857 | 10/1973 | Schrading | 604/356 |
| 3,881,477 | 5/1975 | Von Otto . | |
| 4,055,173 | 10/1977 | Knab . | |
| 4,082,092 | 4/1978 | Foster . | |
| 4,140,105 | 2/1979 | Duvlis . | |
| 4,182,385 | 1/1980 | Williamson | 604/73 |
| 4,223,669 | 9/1980 | Morledge . | |
| 4,250,882 | 2/1981 | Adair | 604/355 |
| 4,252,054 | 2/1981 | Bakels . | |
| 4,446,861 | 5/1984 | Tada . | |
| 4,650,171 | 3/1987 | Howorth . | |

OTHER PUBLICATIONS

Marshall, *The Lancet*, "Bacterial Filter for Suction Apparatus", vol. II, No. 7349, Jul. 1964, p. 21.

*Primary Examiner*—Stephen C. Pellegrino
*Assistant Examiner*—Ralph A. Lewis
*Attorney, Agent, or Firm*—Litman, McMahon & Brown

[57] ABSTRACT

A disposable surgical apparatus for removing potentially harmful materials including fluids, vapors and airborne particles, especially AIDS virus, from an operating zone, during an operation comprising a vacuum generating system that draws the potentially harmful material through a suction manifold mounted on a surface in the proximity of a wound or incision. The suction manifold is incorporated in an elongate strip having an adhesive surface that is adhered to the patient in the vicinity of an incision or the like and that includes a plurality of apertures therealong in flow communication with the vacuum generating system.

18 Claims, 1 Drawing Sheet

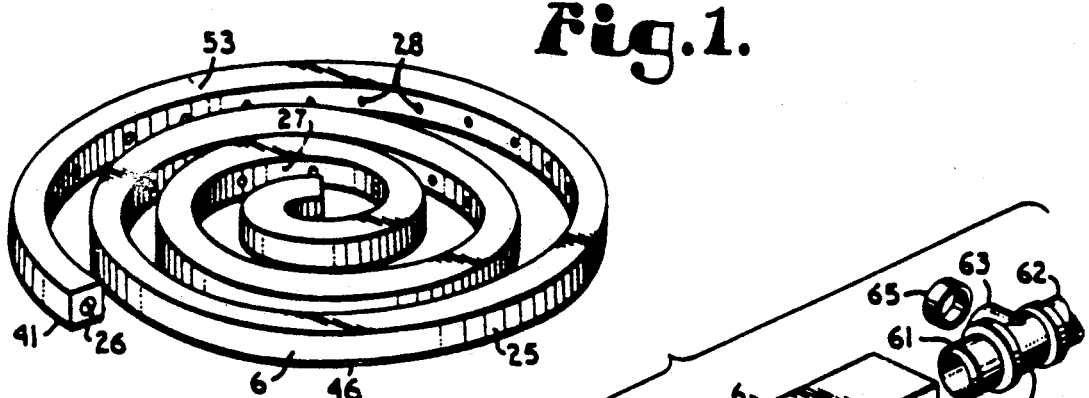
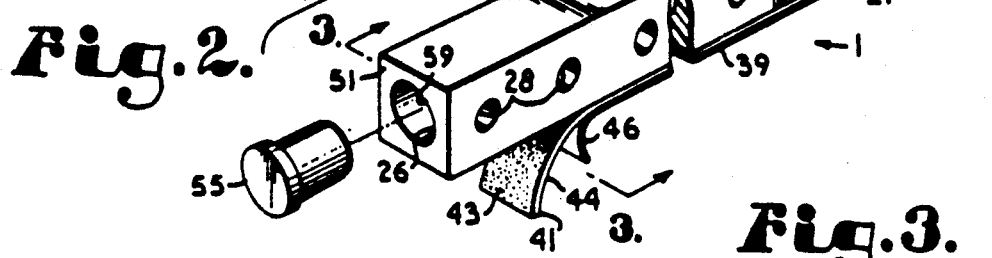
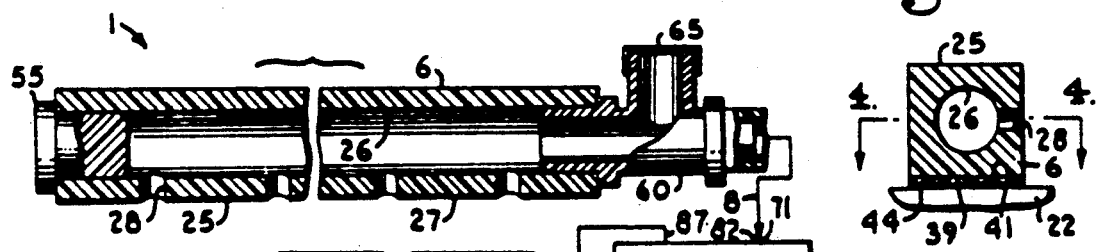
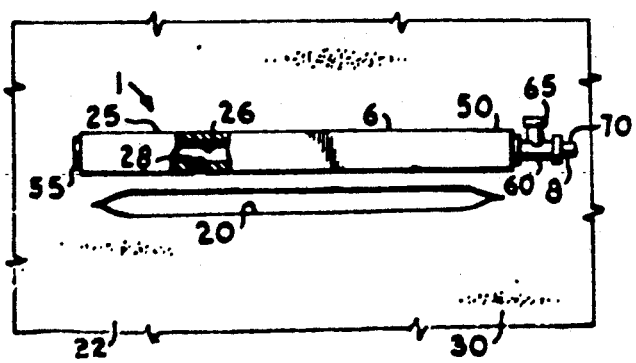
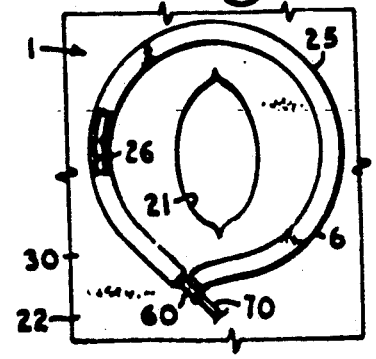

VACUUM STRIP APPARATUS FOR SURGERY

BACKGROUND OF THE INVENTION

1. Field of the Invention

The present invention relates to a surgical ventilating apparatus for protecting members of surgical teams from potentially harmful products that may issue from an operating zone.

2. Description of the Prior Art

Since the advent of the discovery that bacterial and other microorganisms cause diseases and that such microorganisms are easily transmitted to a patient's incision from such sources as a carrier doctor, an unclean instrument or even the air, hospital operating room procedures have incorporated methods to protect the patient by preventing contamination of the operating field. In particular, sources of patient contamination have included bacteria and other microorganisms shed or exhaled by members of the operating team. For example, traditional protective measures have included that the operating team wear face masks. Such protective measures also have included use of ventilating systems that function to prevent contaminants (shed or exhaled by members of the operating team) from entering the surrounding atmosphere and, in particular, from entering the operating field. For example, U.S. Pat. No. 4,055,173 discloses a system for drawing air exhaled by a surgeon and the like away from the surgeon's face so as to limit contamination of the patient.

Although the prior art has included numerous measures to protect patients from contamination originating with the members of the surgical team, there have been few improvements in the prior art to help protect members of the surgical team from airborne contaminants and the like originating with that portion of the patient exposed in the operating field.

Contaminants of concern to members of surgical teams can and do include the Acquired Immunodeficiency Syndrome (AIDS) virus, a disease for which there is currently no effective cure. Thus, the risk of contracting AIDS has created substantial new and deadly problems for the surgeons and other operating room staff. Further, the current spreading epidemic of AIDS has imposed serious health risks on other health care workers subjected in any way to AIDS contaminated blood and body fluids. However, such risks are particularly high for surgeons in all subspecialties and for other operating room personnel, since many operations require drilling, reaming, cutting or like processes and such processes create an aerosol of the patient's blood, tissue, bone or the like that becomes airborne. Aerosols of this type contain live virus, including AIDS virus, when such is present in the patient.

Once a contaminated aerosol subsequently settles on a mucus membrane or open wound of a doctor or nurse, they may be infected by the virally transmitted disease (including AIDS). Accidental contamination with airborne aerosols of blood and body fluids of patients having other diseases, such as hepatitis B, may also be communicated by such a mechanism.

Studies have also identified other sources of risk to include inadvertent inoculations through scalpel laceration, needle puncture, splashing and contact of contaminated serum or body fluids with an open wound. Such studies are described in J. Bartlett, "Testing for HIV Infection: Recommendations for Surgeons", Vol. 73, No. 3, *American College of Surgeons Bulletin* and G. Telford, et al., "A Protocol to Reduce the Risk of Contracting AIDS and Other Blood-Borne Diseases in the OR", March, 1988, *Surgical Rounds for Orthopedics.*

In addition to the traditional measures for protecting patients noted above, guidelines have been proposed to safeguard health care workers in the high risk areas. These guidelines consist mainly of recommendations for safe handling of sharp instruments and also include barrier precautions such as gloves, face shields, impervious masks and gowns, and foot and leg wear. However, such guidelines do not adequately address the risk associated with the effects of spraying blood and the like and the aerosolization of blood, body fluids and tissue during a medical procedure. The production of such aerosols occurs during surgical procedures involving the use of many medical operating tools (especially rotating or sawing power equipment such as high speed drills, saws and reamers of the type used by orthopedic surgeons, neurosurgeons and other surgeons who must penetrate bone and other tissue). While the extent and effects of aerosoled blood, body fluids and tissue during surgical procedures is dependent upon the size, shape and speed of the spray inducing devices, often the microscopic aerosols are found in the air throughout the operating room.

Other safeguard guidelines suggest that preoperative testing be conducted for a presence of risk-producing contaminants. Such testing would, it is thought, by identifying such contaminants, allow surgeons to take special precautions. However, preoperative testing for patients inflicted with the human immunodeficiency virus (HIV), AIDS related complex (ARC) and hepatitis B has encountered legal constraints and is also not always effective in operation. Legal constraints against preoperative testing have arisen because of the controversial nature of such testing. Preoperative testing is also not always effective because of the existence of a "serum negative window" (i.e. early period in the disease cycle when the disease is not easily detectable) between exposure and the time when the virus produces sero positive test results. Further, in emergency situations where low but significant percentages of trauma victims are sero positive there is often no time for preoperative testing. And even if testing does show a positive virus infection of AIDS or a similar disease, the surgery may still require a procedure that will produce an aerosol containing the virus.

Accordingly, it is highly desirable to confine the potential contaminant to the smallest area possible and, thus, minimize its diasemination and ultimate spread to members of the surgical team and other health care workers. This can be accomplished by creating a negative pressure zone in the field of operation which operates to remove the contaminants before they escape into the surrounding atmosphere. For this purpose, it is important that the low pressure zone be generated by a device which is near the wound or incision in the field of operation but which does not impede the dexterity or vision of the surgeon.

SUMMARY OF THE INVENTION

The present invention alleviates a substantial portion of the risk associated with conducting surgery on patients who are inflicted with AIDS and other extremely communicable and hazardous diseases. The invention is intended to be used by such a surgeon, especially when the surgeon knows the patient is infected or is uncertain whether the patient is infected. Use of the invention thereby reduces the risk, particularly that risk associated with surgery on patients who have recently acquired such a disease but who do not test positive or who were not tested at all. The invention is also designed not to unduly encumber the surgeon or hamper vision or dexterity, thereby making use of the invention attractive to the surgeon for all surgeries performed. In particular, an apparatus is provided for reducing the air pressure by creating a vacuum in the vicinity of the surgery, thereby drawing most of the aerosols produced by the surgery (and, consequently any AIDS virus or other microorganism) into the apparatus creating the vacuum. The apparatus comprises a vacuum strip including a hollow and flexible tube that is positioned on and which adheres to the surface of the patient in the proximity of the wound or incision.

The vacuum strip has a plurality of apertures directed outwardly from an inner chamber. The inner chamber of the vacuum strip is connected to a transfer conduit. The transfer conduit is attached, through a liquid separator and high efficiency filter suitable to remove microorganisms, to a vacuum pump system.

The vacuum pump induces a negative pressure in the transfer conduit, vacuum strip and, consequently, in the proximity of the vacuum strip. Air and airborne material and vapor from the region surrounding the wound or incision are, thus, drawn into the vacuum strip through the conduit and into the filter. The filter operates to remove the hazardous materials from the air. The filtered air is then drawn, through a vacuum regulator, into the vacuum pump where it is discharged into a vacuum pump discharge header. As the vacuum strip is located normally near the site of surgery, especially during an aerosol creating process, a substantial amount of the aerosols produced are drawn through the apparatus and the microorganisms are subsequently captured by the filter. The apparatus, including the strip, liquid separator and filter, are disposed of and suitably destroyed after an operation. It is also foreseen that the strip can be used to completely surround the incision or wound during an irrigating procedure or where the patient is bleeding such that contaminated blood and other fluids can be drawn into the apparatus and removed from the site of the operation.

OBJECTS OF THE INVENTION

Therefore, the principal objects of the present invention are: to provide an improved surgical apparatus for facilitating the removal of patient originated microorganisms from a surgical environment; to provide such an apparatus which is disposable; to provide such an apparatus which does not appreciably reduce the ease of access of field of vision by the surgeon to the operating field; to provide such an apparatus which draws a vacuum in the vicinity of the operating field so as to reduce the escape of aerosols, produced by the surgeon acting on the patient, into the general surgical environment; to provide such an apparatus comprising an elongate strip adapted to be adhesively secured to the patient about the surgical site and having multiple apertures along the strip operatively flow connected to a vacuum producing system to draw air, including aerosols with microorganisms therein, and fluids into the apparatus and away from the site and the surgeon; and to provide such an apparatus which is relatively easy to manufacture, relatively inexpensive to produce and that is particularly well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view showing a vacuum strip according to the present invention, in a partially coiled position for storage prior to use.

FIG. 2 is a fragmentary and enlarged perspective view of the apparatus, including the strip, a plug and an adapter.

FIG. 3 is an enlarged cross-sectional elevational view of the strip positioned on a patient, taken along line 3—3 of FIG. 2.

FIG. 4 is an enlarged cross-sectional view of the apparatus, showing the strip attached to a filter and a vacuum pump, taken along line 4—4 of FIG. 3.

FIG. 5 is a top plan view of the apparatus positioned adjacent to an incision in a patient, with portions broken away to show detail thereof.

FIG. 6 is a top plan view of the apparatus utilized to surround an incision in a patient, with portions broken away to show detail thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in detail, the reference numeral 1 generally designates a vacuum strip apparatus according to the present invention. The vacuum strip apparatus 1 generally includes vacuum strip means, that in the present embodiment is illustrated as a strip 6, conduit means, that in the present embodiment, is illustrated as an elongated tube or a conduit 8, fluid collection means such as fluid collection vessel 9, filter means such as filter 10 and a suction pump means such as vacuum pump 12.

FIG. 1 illustrates the strip 6 in a semi-coiled position for storage prior to use. The strip 6 is preferably constructed of a flexible plastic that may be trimmed in length at the time of use to provide a surgeon or other user with a suitable length for positioning around, as seen in FIG. 6, or alongside, as seen in FIG. 5, a surgical site 20 or 21 respectively in a patient's skin 22. The strip 6 comprises an elongate hollow band 25 which has an internal chamber 26 communicating with an outer surface 27 through a plurality of generally evenly spaced and equally sized ports, apertures or openings 28 positioned at spaced locations along the surface 27.

The strip 6 is formed of suitable, moisture resistant and substantially fluid impervious, tubing-like material having sufficient resilience and flexibility to conform to the varying contours of the surface of the skin 22 of a human body 30 to which it is applied.

The openings 28 are spaced and arranged so as to allow any air (or other fluid material surrounding or in contact with the strip 6) with hazardous contaminants therein to be drawn into the vacuum strip apparatus 1. The contaminants may be in aerosols which are formed during a medical operation, and include microorganisms such as bacteria or virus or hazardous chemicals or the like used in industrial manufacturing processes. It is also foreseen that the contaminants may be in the form of a liquid that accumulates inside the area surrounded by the vacuum strip apparatus 1 due to bleeding, irrigation by the surgeon or the like.

Spaced from the openings 28 is a generally flat engagement surface 39 for interfacing the strip 6 with the patient's skin 22 to which the strip 6 will ultimately be attached. Preferably, the strip 6 has a rectangular cross-section and the plane of the engagement surface 39 is generally parallel to a longitudinal axis of the strip 6 and generally perpendicular to the surface 27 associated with the openings 28. A central axis of each of the openings 28 generally lies on a line perpendicular to the longitudinal axis of the strip 6. The strip 6 generally includes an adhesion means, that in the present embodiment is illustrated as double-sided adhesive tape 41. An inner adhesion surface 43 of adhesive tape 41 is secured to the engagement surface 39 and is coated with adhesive material acceptable for medical applications. An outer adhesion surface 44 of the adhesive tape 41 is likewise coated with adhesive material acceptable for medical applications and is provided with an easily removed covering 46 for protection of the outer adhesion surface 44 during storage. Just prior to use, the covering 46 is removed to expose the adhesive surface 44 that is then applied to the skin 22.

Strip segments, such as segment 50 illustrated in FIG. 2 and FIG. 5, may be cut from the strip 6 through a plane such as identified by the line 53 in FIG. 1. The segment 50 may be cut to any desired size for a particular use. Strip segment 50 includes a first end 51 and a second end 52. Once cut to the desired length, a plug 55 of suitable design to fit snugly within the internal chamber 26, is inserted into the first end 51, when the strip 6 is to be used in a linear configuration, as shown in FIG. 5. The chamber 26 is of generally uniform diameter along the entire length thereof. The plug 55, when positioned in the end of the chamber 26, prevents the flow of air through the exposed opening or end port 59 associated with the chamber 26 at the strip first end 51. Insertable into the chamber 26 at the strip second end 52 is a conduit receiving adapter 60 for flow connecting the tubular conduit 8 to the strip segment 50 (gas or liquid) in such a manner as to allow flow of fluid passing through said strip openings 28 and into the internal chamber 26, to flow into an interior lumen associated with the tubular conduit 8. In particular, the conduit-receiving adapter 60 allows air and hazardous contaminants contained therein to be drawn through the strip segment 50 into the tubular conduit 8.

The illustrated adapter 60 is a T-shaped member having a first end 61 frictionally received in the strip chamber 26, a second end 62 around which the conduit 8 is secured such that the conduit 8 is in flow communication with the chamber 26 and a third end 63. The third end 63 may be alternatively capped with a closure cap 65, where the strip 6 is used linearly or in a non-circular fashion as shown in FIGS. 4 and 5 or the cap 65 and plug 55 may be removed and the chamber port 59 (at the strip first end 51) may be connected to the adapter third end 63 to form a circular or continuous configuration of the strip 6, such as is illustrated in FIG. 6. In this manner, the apparatus 1 can be used to completely surround a surgical site 21, also as shown in FIG. 6.

In particular, it is foreseen that a strip segment 50 can be cut of sufficient length to form a dam around a wound or incision, such as the surgical site 21, to collect and evacuate aerosols produced by an operation, liquids used to irrigate or treat the site 21 or any liquid issuing from the site 21, as illustrated in FIG. 6.

Tubular conduit 8 is constructed of any suitable tubular material which is moisture resistant and substantially fluid impervious. The tubular conduit 8, at a first end 70 is connected to the conduit receiving adapter second end 62. A second end 71 of the conduit 8 is sealably connected to a fluid collection vessel 9. Tubular conduit 8 allows air, hazardous contaminants, or liquid containing hazardous contaminants to be transferred from the strip segment 50 to the vessel 9.

The vessel 9 is preferably a collection bottle having an inlet 82 and an outlet 87 at the top thereof and adapted to collect liquids or solid particles drawn from the apparatus 1 by the vacuum pump 12.

The filter 10 is constructed of any suitable high efficiency filtering material which removes microorganisms and other particulate matter from air passing therethrough. The vacuum pump 12 is of any suitable type capable of creating and maintaining a preselected negative pressure at its inlet and discharging to a discharge header 90.

In use, the strip segment 50 is cut, positioned and attached to the skin 22 next to or surrounding a surgical site. The vacuum pump is then operated to induce a negative pressure within the conduit 8 and the strip segment chamber 26 positioned in the operation field. While the surgeon is conducting surgical procedures, air, hazardous contaminants, and liquids, especially aerosols containing blood, tissue, bone and the like, and which may become airborne in the operation field, are drawn into the spaced openings 28 in the strip 6 through the tubular conduit 8, the collection vessel 9 and into the filter 10 whereat substantially all of the non-air components are removed, such that all or a substantial portion of the hazardous contaminants are removed from the air before the air exits the discharge header 90 and maintained in the collection vessel 9 or filter 10.

It is to be understood that while certain forms of the present invention have been illustrated and described herein, it is not to be limited to the specific forms or arrangement of parts described and shown.

What is claimed and desired to be secured by Letters Patent is as follows:

1. A vacuum strip apparatus for use during medical procedures for removing liquids and aerosols containing contaminants released by a patient from the operating room environment; said apparatus comprising:
 (a) vacuum strip means including adhesion means to allow said strip means to be selectively secured in close proximity to a source of liquid and aerosol contaminants; said vacuum strip means having an elongate relatively narrow structure and including at least one aperture therein; said vacuum strip means being flexible at least in a plane generally parallel to said adhesion means such that said vacuum strip means can be secured to a patient by said adhesion means and configured to lie along a selected path on the skin of the patient;

(b) suction pump means flow connected to said strip aperture; said pump means adapted to induce a negative pressure in said aperture so as to draw said contaminants through said aperture; and (c) conduit means for flow connecting said vacuum strip means to said suction pump means.

2. The apparatus according to claim 1 including:

(a) filter means flow connected between said vacuum strip means and said suction pump means for removing contaminants from air drawn through said aperture.

3. The apparatus according to claim 2 including:

(a) fluid collection means flow positioned along said conduit means between said strip means and said filter means for collecting a substantial portion of liquid drawn into the vacuum strip apparatus.

4. An apparatus as set forth in claim 1 wherein said vacuum strip means comprises:

(a) a flexible and resilient hollow tube with an outer surface and an interior chamber spaced from said outer surface;

(b) said outer surface having a plurality of spaced apertures including said one aperture therealong directed radially outwardly; each spaced aperture having a central axis which lies on a line generally perpendicular to a longitudinal axis of said hollow tube;

(c) said outer surface having a generally flat engagement portion adapted to adhere to the patient such that said apertures are in close proximity with the source of contamination, the plane of said engagement portion being generally perpendicular to a face of said outer surface having the spaced apertures therein;

(d) said adhesion means providing releasable adherence of said hollow tube to said patient in close proximity with the source of contamination; and (e) coupler means to connect a first end of said hollow tube to said conduit means.

5. The apparatus as set forth in claim 4 wherein:

(a) said tube is segmentable into sections of various length to allow for variance in size of a surgical site.

6. An apparatus as set forth in claim 4 wherein:

(a) said adhesion means includes double-sided adhesive tape applied to said engagement portion; said adhesive tape having an inner adhesion surface for adhering to said engagement portion and an outer adhesion surface for securing to the patient in close proximity to the source of the contaminants, said outer adhesion surface covered with a removable non-stick covering during storage.

7. A vacuum strip apparatus for use during medical procedures for removing liquids and aerosols containing contaminants released by a patient from the operating room environment; said apparatus comprising:

(a) vacuum strip means having;

(1) a flexible and resilient tube with an outer surface and an interior surface spaced therefrom; said tube having a central axially extending chamber; said tube having a first end and a second end; both of said first and second ends having openings therein for communicating with said chamber;

(2) said tube outer surface having a plurality of apertures directed generally radially and spaced therealong and said apertures flow communicating with said chamber; each of said apertures having a central axis which lies on a line generally perpendicular to a longitudinal axis of said tube;

(3) said tube outer surface having a generally flat engagement portion adapted to adhere to a patient such that said openings are in close proximity with a source of contamination during use; said engagement portion being generally perpendicular to a face of said tube outer surface having the apertures therein;

(4) adhesion means on said engagement portion and adapted to provide for releasable adherence of said hollow tube to said patient in close proximity with the source of contamination; said adhesion means including double-sided adhesive tape applied to said engagement portion; said adhesive tape having an inner adhesion surface for adhering to said engagement portion, and an outer adhesion surface for securing to the patient, said outer adhesion surface covered with a removable non-stick covering during storage;

(5) coupler means comprising a T-shaped member; said member having port adapted to be joined to either end of said tube and flow connect with said chamber through said openings;

(6) plug means for allowing selective plugging of one of said ports of said T-shaped member and one of said openings of said tube, such that said apparatus may be selectively placed in a first configuration wherein said member is connected to both of said openings of said tube through respective ports and alternatively placed in a second configuration wherein said member is connected through only one of said ports to one of said openings of said tube and said plug means plugs both an opposite opening of said tube and a second of said ports;

(b) suction pump means flow connected to said strip apertures; said pump means adapted to induce a negative pressure in said apertures so as to draw the contamination therethrough;

(c) filter means flow positioned between said vacuum strip means and said suction pump means for removing contaminants from a substantial portion the air drawn through said suction pump means;

(d) conduit means for flow connecting said vacuum strip means to said pump means; and (e) fluid collection means flow positioned along said conduit means between said strip means for collecting a substantial portion of liquid drawn into said apparatus.

8. A method of removing liquids and aerosols containing contaminants issuing from a source of contamination including a surgical site, comprising the steps of:

(a) providing a flexible vacuum strip apparatus having an adhesive strip along one side thereof and being operably connected to a source of vacuum and to an aerosol and liquid collection system;

(b) releasably affixing said vacuum strip apparatus to a patient by flexing said apparatus and by adhering said adhesive strip to the body of a patient along a preselected path in close proximity to the source of contamination; and (c) inducing a vacuum in vacuum strip apparatus whereby airborne liquids and aerosols containing contaminants are drawn into said vacuum strip apparatus and conveyed to the collection system.

9. The method according to claim 8, including the steps of:
(a) fabricating said vacuum strip apparatus from medically acceptable materials; and
(b) affixing said vacuum strip apparatus to a patient in surrounding relationship to a surgical site of the patient prior to inducing said vacuum.

10. The method according to claim 8 including the steps of:
(a) prior to inducing said vacuum, positioning said vacuum strip apparatus in a damming configuration about said site, whereby liquids from said site are drawn into said vacuum strip apparatus by said vacuum source and collected in said collecting system.

11. A vacuum strip apparatus for use during medical procedures for removing liquids and aerosols containing contaminants released by a patient from an operating room environment, said apparatus comprising:
(a) vacuum strip means including adhesion means to allow said strip means to be selectively secured in close proximity to a source of the contaminants, said vacuum strip means including:
 (1) a flexible and resilient hollow tube having opposite ends, an outer surface, and an interior chamber spaced from said outer surface;
 (2) said outer surface having a plurality of spaced openings therealong directed radially outwardly, each opening having a central axis which lies on a line generally perpendicular to a longitudinal axis of said hollow tube;
 (3) said outer surface having a generally flat engagement portion adapted to adhere to the patient such that said openings are in close proximity with a source of contamination, the plane of said engagement portion being generally perpendicular to a face of said outer surface having the spaced openings therein; and
 (4) said adhesion means providing releasable adherence of said hollow tube to said patient in close proximity with the source of contamination;
(b) suction pump means flow connected to said tube, said pump means being adapted to induce a negative pressure in said openings to draw said contaminants therethrough;
(c) conduit means for flow connecting said tube to said pump means;
(d) coupler means to connect said tube to said conduit means, said coupler means including a T-shaped member, said member having ports adapted to be joined to either end of said tube and flow connect with said openings through said chamber; and
(e) plug means for selectively plugging one of said ports of said member and one end of said tube such that said apparatus may be selectively placed in a first configuration wherein said member is connected to opposite ends of said tube through said ports and alternatively placed in a second configuration wherein said member is connected by only one of said ports to one end of said tube and said plug means plugs both an opposite end of said tube and a second of said ports.

12. A vacuum strip apparatus for collecting liquids and aerosols emanating from a surgical site and comprising:
(a) an elongated and relatively narrow tubular vacuum strip having a patient engagement surface and an exterior wall;
(b) said strip including a plurality of spaced apart apertures being formed through said exterior wall in spaced relation to said patient engagement surface;
(c) adhesive means located along said strip patient engagement surface adapted to secure said vacuum strip to a patient during use; said vacuum strip being generally flexible at least in a plane parallel to said adhesive means to allow flexing of said vacuum strip into a preselected configuration about said surgical site prior to securing of said vacuum strip to the patient and said vacuum strip being removably held in said configuration by said adhesive means after said vacuum strip is secured to the patient; and
(d) suction pump means flow connected to said vacuum strip to draw air through said apertures to thereby collect liquids and aerosols emanating from said surgical site.

13. An apparatus as set forth in claim 12 and including:
(a) branched tubular coupler means having a first port, a second port, and a third port;
(b) said strip being flexible, having opposite ends, and being positioned in a loop configuration to thereby surround a surgical site, said opposite ends of said strip being flow connected respectively with said first and second ports; and
(c) said pump means being flow connected with said third port.

14. An apparatus as set forth in claim 12 and including:
(a) collection means flow connected between said strip and said pump means to receive said liquids and aerosols from air drawn through said apertures.

15. An apparatus as set forth in claim 12 and including:
(a) filter means flow connected between said strip and said pump means to remove said liquids and aerosols from air drawn through said apertures.

16. An apparatus as set forth in claim 12 and including:
(a) adhesive means positioned on said patient engagement surface of said strip to removably attach said strip to skin of a patient.

17. An apparatus as set forth in claim 12 wherein:
(a) said strip is formed of a material which is capable of being cut into a segment of a selected length.

18. A vacuum strip apparatus for collecting liquids and aerosols emanating from a surgical site and comprising:
(a) an elongated tubular vacuum strip having a patient engagement surface and an aperture wall;
(b) a plurality of spaced apart apertures formed through said aperture wall in spaced relation to said patient engagement surface;
(c) suction pump means flow connected to said strip to draw air through said apertures to thereby collect liquids and aerosols emanating from said surgical site;
(d) branched tubular coupler means having a first port, a second port, and a third port;
(e) said vacuum strip having opposite ends sized for flow connecting with said first and second ports, at least one of said ends being flow connected to said first port;

(f) said pump means being flow connected to said third port; and (g) plug means adapted for selectively sealing another of said ends of said strip and said second port whereby said vacuum strip may be selectively placed in a first configuration with said opposite ends of said strip flow connected to said first and second ports and alternatively in a second configuration with one of said ends flow connected to said first port and said second port and said other end of said strip being sealed by said plug means.

* * * * *